Figure 1:
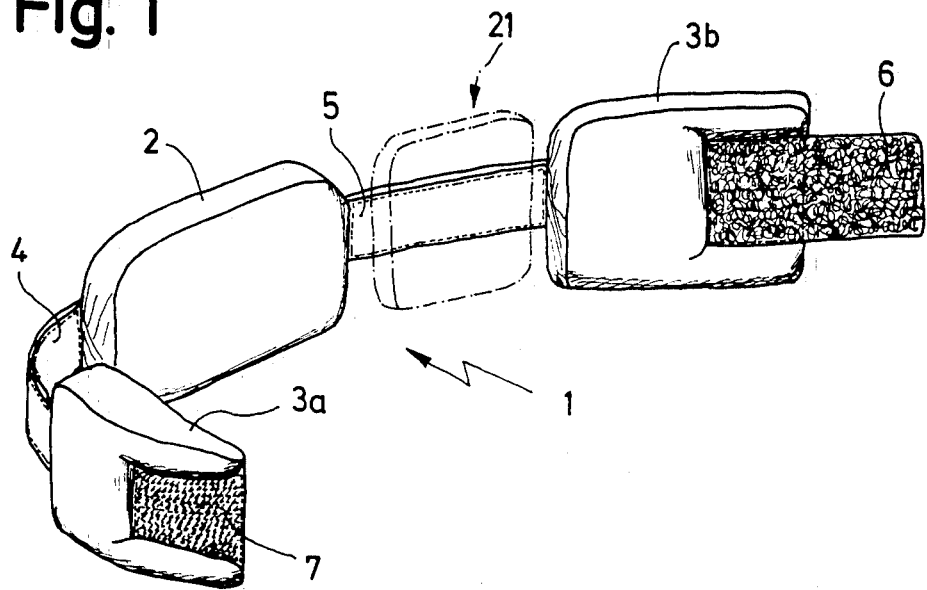

United States Patent [19]

Auracher

[11] Patent Number: 4,576,150
[45] Date of Patent: Mar. 18, 1986

[54] ORTHOPAEDIC SUPPORT FOR THE HEAD AND NECK

[76] Inventor: Walter Auracher, Colmarer Strasse 45, 7000 Stuttgart 40, Fed. Rep. of Germany

[21] Appl. No.: 584,649

[22] Filed: Feb. 29, 1984

[30] Foreign Application Priority Data

Mar. 10, 1983 [DE] Fed. Rep. of Germany ....... 3308571

[51] Int. Cl.⁴ .............................................. A61H 1/02
[52] U.S. Cl. .............................. 128/75; 128/DIG. 23; 128/DIG. 15
[58] Field of Search ............... 128/75, 87 R, DIG. 15, 128/DIG. 23

[56] References Cited

U.S. PATENT DOCUMENTS 3,285,243 11/1966 Yellin ..................................... 128/75
3,477,425 11/1969 Grassl ..................................... 128/75

Primary Examiner—Richard J. Apley
Assistant Examiner—Alan W. Cannon
Attorney, Agent, or Firm—Shenier & O'Connor

[57] ABSTRACT

The invention relates to an orthopaedic support for the head and neck comprising a pad placed circularly around a patient's neck and releasable fastener elements attached thereto. In order to avoid the patient perspiring under such a support and thereby avoid the support becoming damp the pad consists of individual, separate pad elements flexibly connected to each other. In particular, the pad elements may be separated and spaced from each other and be joined to each other by flexible tapes.

3 Claims, 5 Drawing Figures

U.S. Patent Mar. 18, 1986 Sheet 2 of 2 4,576,150

ORTHOPAEDIC SUPPORT FOR THE HEAD AND NECK

The invention relates to an orthopaedic support for the head and neck comprising a pad to be placed circularly around a patient's neck and releasable fastener elements attached thereto.

Known head and neck supports of this type obtainable from specialized dealers have a large, one-piece pad which fits closely around the patient's entire neck. It is not possible for air to reach the skin covered by the pad and the patient will feel constricted and perspire heavily so that the support will become damp and, with time, take on an unpleasant odour. It is often the case that the support prescribed by the doctor will then no longer be worn.

The object of the invention is to remedy the deficiencies described above and to design a support for the head and neck of the type in question such that any undesirable perspiring around the patent's neck will be avoided while still maintaining the therapeutic effect.

The object is accomplished according to the invention in that the pad consists of individual, separate pad elements which are flexibly connected to each other.

This will enable air to circulate between the separate pad elements and this circulation of air will also reach under the edge areas of the individual pad elements. This will avoid the pad elements becoming damp due to perspiration in the neck region.

Figure 2:
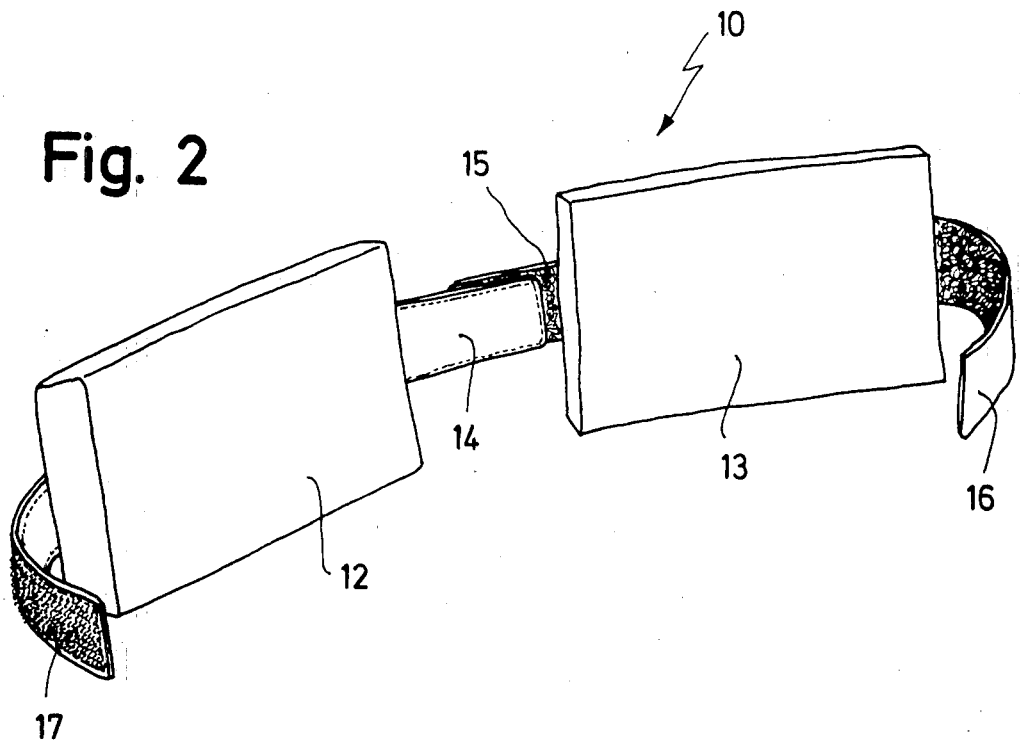
Figure 3:
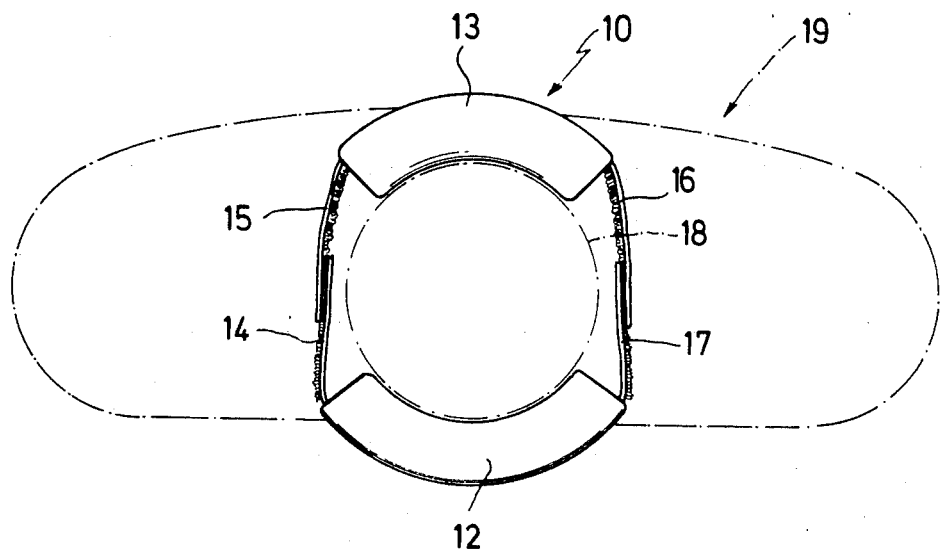
Figure 4:
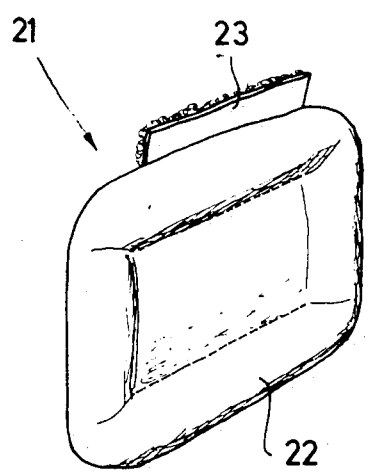
Figure 5:
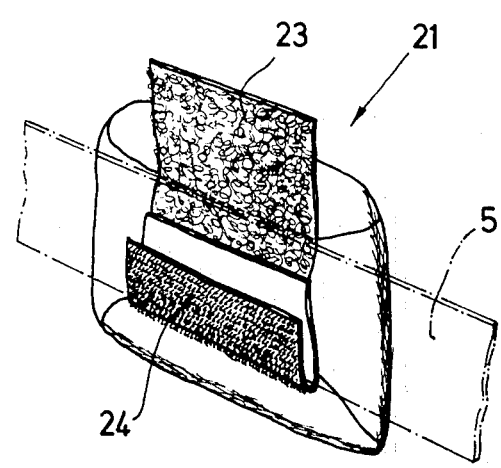

The following description of preferred embodiments of the invention serves to explain the invention in more detail, in conjunction with the attached drawings which show:

FIG. 1 a first embodiment of an orthopaedic support for the head and neck;

FIG. 2 a second embodiment of a support for the head and neck;

FIG. 3 a schematic plan view of the support for the head and neck shown in FIG. 2 worn around a patient's neck;

FIG. 4 a front view of an additional pad element for the support shown in FIG. 1 and FIG. 5 a rear view of the pad element shown in FIG. 4.

The orthopaedic support 1 for the head and neck illustrated in FIG. 1 has as essential components a plurality of separate pad elements 2, 3 and 3a which are displaceably connected to each other by flexible tapes 4, 5. When the support 1 is worn the pad elements rest against the patient's neck, pad element 2 beneath the chin and the pad element 3 made up of two parts, 3a and 3b at the nape of the neck. The two pad element parts 3a and 3b thereby overlap to a greater or lesser degree depending on the size of the patient's neck. For this purpose, the pad element parts 3a, 3b are tapered or stepped in the area where they overlap so that they are, together, no thicker than the pad element parts in the areas where they are not tapered or stepped. The pad element parts 3a, 3b are connected to each other by a self-adhesive fastener tape 6 attached to one of these elements and a self-adhesive fastener member 7 which is complementary to the tape 6 and is attached to the other pad element. Once the support 1 has been placed around the patient's neck the self-adhesive fastener tape 6 is pressed onto the self-adhesive fastener member 7 and the support thereby fastened together. The tapes 4, 5 joining two pad elements to each other are located on the side of the pad elements facing away from the patient's neck (outer side). When the support 1 is worn a gap will remain between the neck and the tapes 4, 5, through which air can circulate. Since the tapes 4, 5, as shown in FIG. 1, are attached to the outer sides of the pad elements 2, 3, the edge areas facing away from the place of attachment rest only lightly against the patient's neck so that a movement of air can also take place underneath these areas. Altogether, it is therefore guaranteed that the head and neck support 1 is well ventilated, the patient no longer perspires and the support will not become damp.

The modified embodiment of a support for the head and neck illustrated in FIG. 2 comprises two pad elements 12, 13 which are spaced from each other and connected by flexible self-adhesive fastener tapes 14, 15. Additional self-adhesive fastener tapes 16, 17 are attached to the sides of the pad elements 12, 13 opposite the self-adhesive fastener tapes 14, 15. The tapes 14, 15, 16 and 17 are again attached to the outer sides, i.e. to the sides of the pad elements 12, 13 facing away from the patient's neck. The two pad elements 12, 13 are detachably connected to each other by the two tapes 14, 15. The pad element 12 serves as a chin support, the pad element 13 as a support for the nape of the neck.

FIG. 3 is a schematic illustration of the neck and head support of FIG. 2 worn around the neck 18 of the patient 19. In contrast to the embodiment of the support 1 illustrated in FIG. 1 the pad element 13 resting against the nape of the neck is in one piece. The support 10 for the head and neck is therefore fastened not at the nape of the neck but laterally, approximately under the patient's ear, by pressing together the relevant self-adhesive fastener tapes, for example tapes 16, 17. Since—as clearly shown in FIG. 3—the tapes 14, 15, 16 and 17 are attached to the outer sides of the pad elements 12, 13 these tapes do not lie against the patient's neck and the head and neck support 10 is well ventilated in the manner described above in connection with the embodiment shown in FIG. 1.

For customary complaints, such as any disorders of the cervical vertebrae, it is sufficient to support the head beneath the chin and at the nape of the neck. This type of support is fully guaranteed by the supports 1, 10 according to FIGS. 1 and 2. If, in special cases, lateral support of the head is necessary in the area beneath the ear, special additional pads can be attached to the flexible tapes joining the pad elements located beneath the chin and at the nape of the neck. This is indicated in FIG. 1 in connection with an additional pad element 21 which is illustrated in detail in FIGS. 4 and 5. The front side of the pad element 21 may have the bead-like edge area 22 shown in FIG. 4. Two self-adhesive fastener tapes 23, 24 which cooperate with each other are attached to the back of the pad element 21 (FIG. 5). These two self-adhesive fastener tapes 23, 24 are fastened around the tape 5 joining the two pad elements 2, 3 to each other. The pad element 21 is therefore secured between the pad elements 2, 3—vide FIG. 1. Since gaps are also left between the pad element 21 and the adjacent pad elements 2, 3 and the self-adhesive fastener tapes 23, 24 are attached to the back of the pad element 21, good ventilation is guaranteed around the patient's neck in the region of pad element 21.

The pad elements 2, 3, 12, 13 and 21 may consist in the known way of known padding material, especially foamed materials. Particularly suitable is the relatively hard, foamed plastic sold under the brand name of "Plastazote", which is to a large extent dimensionally stable and stiff and may be deformed by using heat. The actual padding material will be covered in the customary way by tricot hose fabric or the like, for example of silk or cotton. Plastic foils or plastic coatings of the types not irritating to the skin may also be used. The pad elements may have a thickness of between 5 and 30 mm. Their height, which determines their effective support, may be between 6 and 12 cm for the chin support and between 6 and 18 cm for the support for the nape of the neck (pad elements 2 and 3). The pad elements may, if required, be adapted to suit a patient's particular anatomy. For example, the pad element serving as chin support may have a slightly concave curve along its upper edge. Other arrangements of the pad elements relative to each other and differing from that illustrated in the drawings are, of course, possible.

The tapes connecting the pad elements with each other may be designed in the known way as rubber, belt, leather or plastic tapes or straps. The essential feature is that they are secured to the pad elements at a point "off the neck".

The fastener elements for fastening the described support for the head and neck and for securing additional pad elements 21 are preferably designed as self-adhesive fasteners. It is, however, also possible to use button, slide, buckle, magnet, belt, tie, strap and hook fasteners. The pad elements may thereby be fastened under the chin, at the nape of the neck or also laterally under the patient's ear.

I claim:

1. An orthopaedic support for the head and neck of a patient comprising a chin pad element having a face for engaging the wearer's neck in the chin region thereof, a nape pad element for engaging the wearer's neck in the nape region thereof, each of said chin and nape pad elements being so dimensioned as to engage the wearer's neck over substantially the entire height thereof, a pair of flexible tapes attached to said chin and nape pad elements for holding said chin and nape elements in spaced relationship when said support is in operative position on a patient's neck, said tapes being narrower than the height of the patient's neck, said tapes bridging the spaces between said chin and nape pads, releasable fastener elements for releasably holding said support in said operative position, and additional pad elements detachably connected to the portions of said tapes bridging said spaces between said chin and nape pad elements.

2. A support as in claim 1 in which said tapes are arranged on the reverse sides of said chin and nape pad elements from said faces.

3. A support as in claim 1 in which said nape pad element is made up of two overlapping parts, and in which said fastener elements connect said overlapping parts.

* * * * *